United States Patent [19]

Hanifin, Jr. et al.

[11] 4,254,048
[45] Mar. 3, 1981

[54] SUBSTITUTED PHENYL ALKYLIDENE ACETOACETONITRILES

[75] Inventors: John W. Hanifin, Jr., Suffern; David N. Ridge, Upper Grandview, both of N.Y.

[73] Assignee: American Cyanamid Company, Stamford, Conn.

[21] Appl. No.: 104,509

[22] Filed: Dec. 17, 1979

[51] Int. Cl.³ ................... A61K 31/275; C07C 121/76
[52] U.S. Cl. ............................ 260/465 F; 260/438.1; 260/465 E; 424/304
[58] Field of Search ............. 260/465 F, 465 E, 438.1; 424/304

[56] References Cited

U.S. PATENT DOCUMENTS

| | | | |
|---|---|---|---|
| 4,061,767 | 12/1977 | Ertel et al. | 424/282 |
| 4,173,650 | 11/1979 | Hanifin, Jr. et al. | 424/304 |

*Primary Examiner*—Dolph H. Torrence
*Attorney, Agent, or Firm*—Edward A. Conroy, Jr.

[57] ABSTRACT

Substituted-phenyl alkylidene acetoacetonitriles which are useful as anti-inflammatory agents and as inhibitors of the progressive joint deterioration characteristic of arthritic disease.

12 Claims, No Drawings

SUBSTITUTED PHENYL ALKYLIDENE ACETOACETONITRILES

DESCRIPTION OF THE INVENTION

This invention is concerned with compounds of the formula:

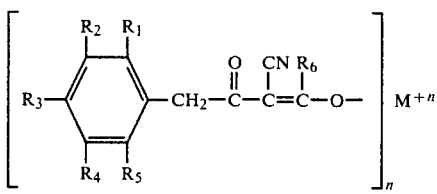

wherein $R_1$, $R_2$, $R_3$, $R_4$ and $R_5$ are each selected from the group comprising hydrogen, halogen, lower alkyl ($C_1$-$C_4$), lower alkoxy ($C_1$-$C_4$), trifluoromethyl and trichloromethyl; $R_6$ is lower alkyl ($C_1$-$C_4$); M is hydrogen or a pharmaceutically acceptable cation; and n is an integer 1, 2, or 3.

The useful pharmaceutically acceptable salts of the compounds of the above structural formula wherein M is hydrogen are those with pharmacologically acceptable metal cations, ammonium, amine cations or quaternary ammonium cations. Preferred metal cations are those derived from the alkali metals, e.g. lithium, sodium and potassium, and from the alkaline earth metals, e.g. magnesium and calcium, although cationic forms of other metals, e.g. aluminum, iron, zinc and in particular copper are within the scope of this invention.

Pharmacologically acceptable amine cations and those derived from primary, secondary or tertiary amines such as mono-, di- or trimethylamine, ethylamine, dibutylamine, triisopropylamine, N-methylhexylamine, declyamine, dodecylamine, allylamine, crotylamine, cyclopentylamine, dicyclohexylamine, mono- or dibenzylamine, α- or β-phenylethylamine, ethylenediamine, diethylenetriamine, and aryliphatic amines containing up to and including 18 carbon atoms, as well as heterocyclic amines, e.g. piperidine, morpholine, pyrrolidine, piperazine and lower alkyl derivatives thereof, e.g. 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g. mono-, di- or triethanolamine, ethyldiethanolamine, N-butylethanolamine, 2-amino-1-butanol, 2-amino-2-ethyl-1,3-propanediol, 2-amino-2-methyl-1-propanol, tris (hydroxymethyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

The compounds of the present invention may be prepared according to the following Flowchart A.

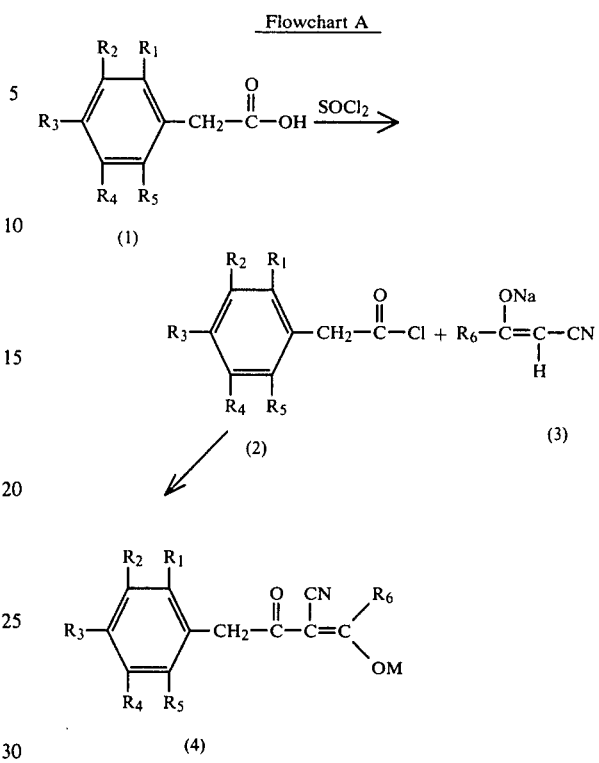

In accordance with Flowchart A an appropriate phenylacetic acid (1) is refluxed with thionyl chloride for several hours, giving the corresponding phenylacetyl chloride (2), which is reacted with α-cyanoketone sodium enolate (3) in a solvent such as tetrahydrofuran for several hours, then after removal of the solvents, the residue in aqueous suspension is acidified and extracted into methylene chloride. Evaporation of this extract gives the products (4) where $R_1$, $R_2$, $R_3$, $R_4$, $R_5$, $R_6$ and M are as described above.

DETAILED DESCRIPTION OF THE INVENTION

The compounds of the present invention have been found to be highly useful for meliorating inflammation and inhibiting joint deterioration in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active ingredient for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active ingredient may be administered in any convenient manner such as by the oral, intravenous, intramuscular, topical or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, phenyl mercuric nitrate, benzalkonium chloride, phenethyl alcohol, p-chlorophenyl-α-glycerol ether, methyl and propyl parabens, and thimerosal. As a practical matter it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The compounds of this invention are equally adapted to intravenous administration when diluted with water or diluents employed in intravenous therapy such as isotonic glucose in appropriate quantities. For intravenous use, initial concentrations down to about 0.05 to 0.25 mg./ml. of active compound are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The following test shows the activity of representative compounds of this invention against chronic inflammation in adjuvant induced arthritis which is accompanied by joint destruction. Groups of three Royal Hart, Wistar strain rats weighing 200±10 grams each, were injected intradermally in the right hind paw with Freund's adjuvant (dried human tubercle bacilli in a mineral oil vehicle) at a dose of 2 mg./kg. of body weight. Test compound was administered orally in a 1.5% starch vehicle at various doses once daily on days 0 through 13 post challenge. Control rats were treated in a similar manner, but given only starch vehicle. On the 14th and 21st day post challenge the diameter of the injected paw (primary lesion) was measure x by micrometer caliper. The volume of inflamed paws were estimated from these measurements and the results are expressed as percent inhibition of swelling as compared to controls. At the same time, the other inflamed sites, such as ears, paws and tail (secondary lesions) were observed and each rat was graded as to degree of inflammation and swelling present. The grading is based on a scale of 0 to 24, where 0 represents a complete absence of induced arthritic nodules and 24 represents the maximum degree of inflammation. The mean grade for each treated group is calculated and the effects of each compound are expressed as percent inhibition of the control grade. Table I records the results of tests conducted with a typical compound of the present invention. This compound appears to suppress the progression of the arthritis and associated joint deterioration.

TABLE I

The Effect of Anti-inflammatory Agents on Adjuvant Induced Arthritis in Rats

| Compound | Oral Dose mg./kg. body weight | Dead/-Treated at 21 Days | Mean Weight Gain (grams) | | % Inhibition Swelling (Primary Lesion) | | % Inhibition of Control Grade (Secondary Lesion) | |
|---|---|---|---|---|---|---|---|---|
| | | | Day 14 | Day 21 | Day 14 | Day 21 | Day 14 | Day 21 |
| 4-(p-Chlorophenyl)-2-(1-hydroxyethylidine)acetoacetonitrile | 25 | 6/21 | 41 | 21 | 68* | 17 | — | — |
| Normal Rats | — | 8/186 | 77 | 112 | — | — | — | — |
| Adjuvant Controls | — | 53/630 | 36 | 31 | 0 | 0 | 0 | 0 |

*Significantly different from adjuvant controls.

Adjuvant induced experimental polyarthritis is a specific system disease of the rat which shares interesting similarities with rheumatoid arthritis. Specifically, the histology of the two diseases bears a remarkable resemblance as shown by C. M. Pearson et al., Am. J. Path. 42, 73 (1963). E. M. Glenn, Am. J. Vet. Res. 27 (116), 339 (1966) has classified adjuvant induced polyarthritis as a crippling and permanent deformity resulting from diffuse connective tissue involvement around certain susceptible joints in the rat. Zahiri et al, Can. Med. Ass. J. 101, 269 (1969) have shown that the fusiform swelling of the distal joints is associated with edema, congestion and synovitis including pannus formation, all of which precede with ultimate destruction of bone and cartilage. Furthermore, Zahiri et al. indicate that the cartilage destruction in the joint is due to an invasive pannus which originates in the marginal synovium and extends across the articular surface to erode it. When nonsteroidal, anti-inflammatory agents such as indomethacin inhibit arthritic paw swelling, which is composed of inflammatory cell infiltrates, they have also been shown to prevent joint and bone deterioration [see S. Wong et al., J. Pharm. & Exp. Ther. 185, 127 (1973) and G. R. Bobalick et al., Agents and Actions 4, 364 (1974)]. The most pertinent reference showing the relationship between arthritis and joint deterioration is an X-ray analysis of adjuvant arthritis in the rat by Blackham et al., Agents and Actions 7, 145 (1977). In a similar manner, inhibition of the progress of arthritis in paws of rats treated with the compounds of this invention also lessens associated joint deterioration.

ml. (83.5 g.) of 5-methyl isoxazole is added dropwise. After addition is complete the reaction is cooled in ice and the solid is filtered, washed with ether and dried giving 57.18 g. of cyanoacetone sodium enolate.

A 100 ml. portion of thionyl chloride is added to 51 g. of p-chlorophenylacetic acid and the mixture is refluxed on a steam bath for 3 hours. The thionyl chloride is removed on a rotary evaporator and the resulting oil is distilled under a water aspirator at 12 mm. giving 51.41 g. of p-chlorophenylacetyl chloride as a pink liquid.

A 9.45 g. portion of p-chlorophenylacetyl chloride followed by 50 ml. of tetrahydrofuran is added to a mixture of 15.76 g. of cyanoacetone sodium enolate in 50 ml. of tetrahydrofuran. The mixture is stirred overnight, then the solvent is removed on a rotary evaporator. The solid is taken up in 100 ml. of water, acidified with concentrated hydrochloric acid and extracted with three 100 ml. portions of methylene chloride. The extracts are combined and extracted with three 100 ml. portions of saturated aqueous sodium bicarbonate. These extracts are combined and acidified with 12N hydrochloric acid, giving an oil. This mixture is extracted with methylene chloride. The extract is dried over magnesium sulfate, filtered through diatomaceous earth and reduced in volume on a steam bath giving the desired product as an oil which crystallizes on standing and after recrystallization from hexanes, then aqueous ethanol has a m.p. 50°–53° C.

Following the general procedure of Example 1, other representative compounds of this invention, such as those found in Table II, may be prepared.

TABLE II

| | (1) Phenyl Acetic Acid | (2) Phenyl Acetyl Chloride | (3) Cyanoacetone Sodium Enolate | (4) Phenyl Hydroxyethylidene Acetoacetonitrile | m.p. 0°C. |
|---|---|---|---|---|---|
| Example | | | | | |
| 2 | $R_1, R_3, R_4, R_5 = H$<br>$R_2 = Cl$ | $R_1, R_3, R_4, R_5 = H$<br>$R_2 = Cl$ | $R_6 = H$ | $R_1, R_3, R_4, R_5, M = H$<br>$R_6 = CH_3$<br>$R_2 = Cl$ | 60–62 |
| 3 | $R_1, R_2, R_4, R_5 = H$<br>$R_3 F$ | $R_1, R_2, R_4, R_5 = H$<br>$R_3 = F$ | $R_6 = CH_3$ | $R_1, R_2, R_4, R_5, M = H$<br>$R_6 = CH_3$<br>$R_3 = F$ | 57–59 |
| 4 | $R_2, R_4, R_5 = H$<br>$R_1, R_3 = Cl$ | $R_2, R_4, R_5 = H$<br>$R_1, R_3 = Cl$ | $R_6 = CH_3$ | $R_2, R_4, R_5, M = H$<br>$R_6 = CH_3$<br>$R_1, R_3 = Cl$ | 113–117* |
| 5 | $R_1, R_4, R_5 = H$<br>$R_2, R_3 = Cl$ | $R_1, R_4, R_5 = H$<br>$R_2, R_3 = Cl$ | $R_6 = CH_3$ | $R_1, R_4, R_5, M = H$<br>$R_6 = CH_3$<br>$R_2, R_3 = Cl$ | 85–87* |
| 6 | $R_2, R_3, R_4, R_5 = H$<br>$R_1 = F$ | $R_2, R_3, R_4, R_5 = H$<br>$R_1 = F$ | $R_6 = CH_3$ | $R_2, R_3, R_4, R_5, M = H$<br>$R_6 = CH_3$<br>$R_1 = F$ | 61–64* |
| 7 | $R_2, R_3, R_4, R_5 = H$<br>$R_2 = F$ | $R_1, R_3, R_4, R_5 = H$<br>$R_2 = F$ | $R_6 = CH_3$ | $R_1, R_3, R_4, R_5, M = H$<br>$R_6 = CH_3$<br>$R_2 = F$ | 43–45 |
| 8 | $R_2, R_3, R_4 = H$<br>$R_1, R_5 = Cl$ | $R_2, R_3, R_4 = H$<br>$R_1, R_5 = Cl$ | $R_6 = CH_3$ | $R_2, R_3, R_4, M = H$<br>$R_6 = CH_3$<br>$R_1, R_5 = Cl$ | 123–124* |

*Final product recrystallized from isopropanol.

EXAMPLE 1

4-(p-Chlorophenyl)-2-(1-hydroxyethylidene)acetoacetonitrile

A 54 g. portion of sodium methoxide in 250 ml. of methanol is cooled and stirred in an ice bath while 82

We claim:
1. A compound selected from those of the formula:

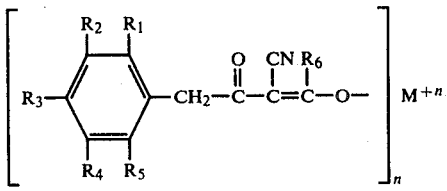

wherein $R_1$, $R_2$, $R_3$, $R_4$ and $R_5$ are each selected from the group comprising hydrogen, halogen, lower alkyl ($C_1$–$C_4$), lower alkoxy ($C_1$–$C_4$), trifluoromethyl and trichloromethyl; $R_6$ is lower alkyl ($C_1$–$C_4$); M is hydrogen or a pharmaceutically acceptable cation; and n is an integer 1, 2, or 3.

2. The compound according to claim 1; 4-(p-chlorophenyl)-2-(1-hydroxyethylidene)acetoacetonitrile.

3. The compound according to claim 1; 4-(m-chlorophenyl)-2-(1-hydroxyethylidene)acetoacetonitrile.

4. The compound according to claim 1; 4-(p-fluorophenyl)-2-(1-hydroxyethylidene)acetoacetonitrile.

5. The compound according to claim 1; 4-(2,4-dichlorophenyl)-2-(1-hydroxyethylidene)acetoacetonitrile.

6. The compound according to claim 1; 4-(3,4-dichlorophenyl)-2-(1-hydroxyethylidene)acetoacetonitrile.

7. The compound according to claim 1; 4-(o-fluorophenyl)-2-(1-hydroxyethylidene)acetoacetonitrile.

8. The compound according to claim 1; 4-(m-fluorophenyl)-2-(1-hydroxyethylidene)acetoacetonitrile.

9. The compound according to claim 1; 4-(2.6-dichlorophenyl)-2-(1-hydroxyethylidene)acetoacetonitrile.

10. The compound according to claim 1; 4-(p-chlorophenyl)-2-(1-hydroxyethylidene)acetoacetonitrile sodium salt.

11. The compound according to claim 1; 4-(m-chlorphenyl)-2-(1-hydroxyethylidene)acetoacetonitrile triethylamine salt.

12. The compound according to claim 1; 4-(p-fluorophenyl)-2-(1-hydroxyethylidene)acetoacetonitrile, cupric salt.

* * * * *